(12) United States Patent
Lau et al.

(10) Patent No.: US 6,211,210 B1
(45) Date of Patent: Apr. 3, 2001

(54) DIPHENYL-1,2,3-THIADIAZOL-3-OXIDES, COMPOSITIONS AND METHODS OF USE

(75) Inventors: Cheuk Kun Lau, Ile Bizard; Chun-Sing Li, Dollard des Ormeaux; Cameron Black, Baie d'Urfe; Michel Therien; Jacques Yves Gauthier, both of Laval, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/561,565

(22) Filed: Apr. 28, 2000

Related U.S. Application Data
(60) Provisional application No. 60/133,025, filed on May 7, 1999.

(51) Int. Cl.⁷ .......................... C07D 285/06; C07F 9/06; A61K 31/38
(52) U.S. Cl. .......................... 514/361; 548/117; 548/127
(58) Field of Search .................. 548/127, 117; 514/361

(56) References Cited

U.S. PATENT DOCUMENTS 5,677,318 * 10/1997 Lau et al. .............................. 514/361

OTHER PUBLICATIONS

Liebigs Ann.Chem., Photolyse der 1.2.3.-Thiadiazol-2-oxide, Braun et al., pp. 1257–1263 (1975).

Drug News and Perspectives, vol. 7; COX–1 and COX–2: Toward the Development of More Selective NSAIDS, Bruno Battistini, et al., pp. 501–512, 1994.

J. of the American Chemical Society, vol. 77, On Acylhydrazones and 1,2,3,–Thiadiazoles, Charles D. Hurd, et al., pp. 5359–5364, May 19, 1955.

\* cited by examiner

*Primary Examiner*—Floyd D. Higel
*Assistant Examiner*—Ebenezer Sackey
(74) *Attorney, Agent, or Firm*—Richard C. Billups; David L. Rose

(57) ABSTRACT

The invention encompasses compounds of Formula I as well as a method of treating COX-2 mediated diseases comprising administration to a patient in need of such treatment of a non-toxic therapeutically effective amount of a compound of Formula I.

I

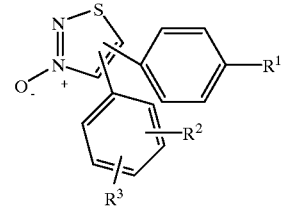

The invention also encompasses certain pharmaceutical compositions for treatment of COX-2 mediated diseases comprising compounds of Formula I.

12 Claims, No Drawings

DIPHENYL-1,2,3-THIADIAZOL-3-OXIDES, COMPOSITIONS AND METHODS OF USE

CROSS-REFERENCE TO RELATED APPLICATIONS

This application is a non-provisional application related to U.S. application Ser. No. 60/133,025, filed on May 7, 1999 priority of which is claimed hereunder.

BACKGROUND OF THE INVENTION

This invention relates to methods of treating cyclooxygenase mediated diseases and certain pharmaceutical compositions therefor.

Non-steroidal, anti-inflammatory drugs exert most of their anti-inflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar anti-inflammatory, antipyretic and analgesic properties to a conventional non-steroidal anti-inflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

A brief description of the potential utilities of COX-2 inhibitors is given in an article by John Vane, *Nature*, Vol. 367, pp. 215–216, 1994 and in an article in *Drug News and Perspectives*, Vol. 7, pp. 501–512, 1994.

SUMMARY OF THE INVENTION

A compound represented by formula I:

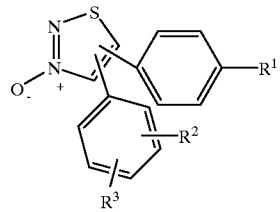

or a pharmaceutically acceptable salt or hydrate thereof wherein:

$R^1$ is selected from the group consisting of:
(a) $S(O)_2CH_3$,
(b) $S(O)_2NHR^4$,
(c) $S(O)_2NHCOCF_3$,
(d) $S(O)(NH)CH_3$,
(e) $S(O)(NH)NH_2$,
(f) $S(O)(NH)NHCOCF_3$,
(g) $P(O)(CH_3)OH$, and
(h) $P(O)(CH_3)NH_2$, $R^2$ and $R^3$ are each independently selected from the group consisting of:
(a) hydrogen,
(b) halo,
(c) $C_{1-6}$alkoxy,
(d) $C_{1-6}$alkylthio,
(e) CN,
(f) $C_{1-3}$fluoroalkyl,
(g) $C_{1-6}$alkyl,
(h) $N_3$,
(i) —$CO_2H$,
(j) —$CO_2$—$C_{1-4}$alkyl,
(k) —$C(R^5)(R^6)$—OH,
(l) —$C(R^5)(R^6)$—O—$C_{1-4}$alkyl, and
(m) —$C_{1-6}$alkyl-$CO_2$—$R^7$;

$R^4$ is selected from the group consisting of H, $C_{1-6}$alkyl, phenyl and benzyl, and $R^5$, $R^6$ and $R^7$ are each independently selected from the group consisting of:
(a) hydrogen, and
(b) $C_{1-6}$alkyl.

Pharmaceutical compositions and methods of treatment are also included.

DETAILED DESCRIPTION OF THE INVENTION

The invention encompasses compounds represented by formula I:

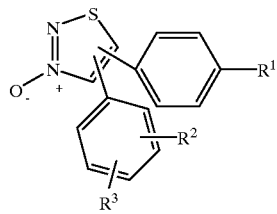

as well as pharmaceutically acceptable salts and hydrates thereof wherein:

R¹ is selected from the group consisting of:
(a) $S(O)_2CH_3$,
(b) $S(O)_2NHR^4$,
(c) $S(O)_2NHCOCF_3$,
(d) $S(O)(NH)CH_3$,
(e) $S(O)(NH)NH_2$,
(f) $S(O)(NH)NHCOCF_3$,
(g) $P(O)(CH_3)OH$, and
(h) $P(O)(CH_3)NH_2$, R² and R³ are each independently selected from the group consisting of:
(a) hydrogen,
(b) halo,
(c) $C_{1-6}$alkoxy,
(d) $C_{1-6}$alkylthio,
(e) CN,
(f) $C_{1-3}$fluoroalkyl,
(g) $C_{1-6}$alkyl,
(h) $N_3$,
(i) —$CO_2H$,
(j) —$CO_2$—$C_{1-4}$alkyl,
(k) —$C(R^5)(R^6)$—OH,
(l) —$C(R^5)(R^6)$—O—$C_{1-4}$alkyl, and
(m) —$C_{1-6}$alkyl-$CO_2$—$R^7$;

R⁴ is selected from the group consisting of H, $C_{1-6}$alkyl, phenyl and benzyl, and R⁵, R⁶ and R⁷ are each independently selected from the group consisting of:
(a) hydrogen, and
(b) $C_{1-6}$alkyl.

As appreciated by those of skill in the art formula I includes, compounds of formulas IA and IB.

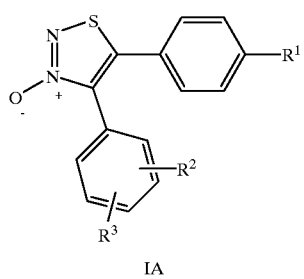

or

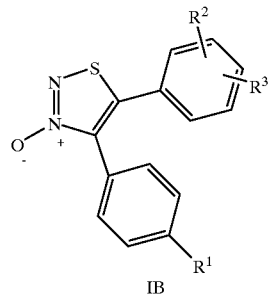

Within the embodiment described above, there is a genus of compounds of formula I wherein R¹ is selected from the group consisting of:
(a) $S(O)_2CH_3$,
(b) $S(O)_2NHR^4$,
(c) $S(O)_2NHCOCF_3$,
(d) $S(O)(NH)CH_3$,
(e) $S(O)(NH)NH_2$,
(f) $S(O)(NH)NHCOCF_3$, R² and R³ are each independently selected from the group consisting of:
(a) hydrogen,
(b) halo,
(c) $C_{1-4}$alkoxy,
(d) $C_{1-4}$alkylthio,
(e) CN,
(f) $C_{1-3}$fluoroalkyl,
(g) $C_{1-4}$alkyl,
(h) —$C(R^5)(R^6)$—OH,
(i) —$C(R^5)(R^6)$—O—$C_{1-4}$alkyl, and
(j) —$C_{1-4}$alkyl-$CO_2$—$R^7$;

R⁴ is selected from the group consisting of hydrogen, $C_{1-4}$alkyl, phenyl and benzyl, and R⁵, R⁶ and R⁷ are each independently selected from the group consisting of:
(a) hydrogen, and
(b) $C_{1-4}$alkyl.

Within this genus there is a class of compounds wherein:

R¹ is selected from the group consisting of:
(a) $S(O)_2CH_3$,
(b) $S(O)_2NHR^4$,
(c) $S(O)_2NHCOCF_3$,
(d) $S(O)(NH)CH_3$, R² and R³ are each independently selected from the group consisting of:
(a) hydrogen,
(b) halo,
(c) $C_{1-3}$alkoxy,
(d) $C_{1-3}$alkylthio,
(e) CN,
(f) $C_{1-3}$fluoroalkyl,
(g) $C_{1-3}$alkyl,
(h) —$C(R^5)(R^6)$—OH,
(i) —$C(R^5)(R^6)$—O—$C_{1-3}$alkyl, and R⁴ is selected from the group consisting of hydrogen, $C_{1-3}$alkyl, phenyl and benzyl;

R⁵ and R⁶ are each independently selected from the group consisting of:

(a) hydrogen, and (b) $C_{1-3}$alkyl.

Within this class there is a sub-class of compounds of Formula Ia

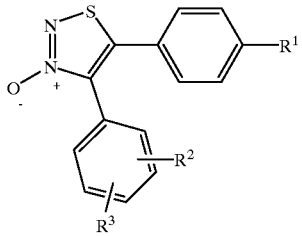

IA

Within this sub-class there is a group of compounds wherein:

$R^1$ is selected from the group consisting of:

(a) $S(O)_2CH_3$, (b) $S(O)_2NHR^4$, (c) $S(O)(NH)CH_3$, (d) $S(O)(NH)NH_2$, $R^2$ and $R^3$ are each independently selected from the group consisting of:

(a) hydrogen, (b) halo, (c) $C_{1-3}$alkoxy, (d) $C_{1-3}$alkylthio, (e) CN, (f) $C_{1-3}$fluoroalkyl, (g) $C_{1-3}$alkyl, (h) —$C(R^5)(R^6)$—O—$C_{1-4}$alkyl, and $R^4$ is selected from the group consisting of hydrogen, $C_{1-4}$alkyl, phenyl and benzyl;

$R^5$ and $R^6$ are each independently selected from the group consisting of:

(a) hydrogen, and (b) $C_{1-3}$alkyl.

Within this group there is a sub-group of compounds wherein:

$R^1$ is selected from the group consisting of:

(a) $S(O)_2CH_3$, (b) $S(O)_2NHR^4$, (c) $S(O)(NH)CH_3$, $R^2$ and $R^3$ are each independently selected from the group consisting of:

(a) hydrogen, (b) halo, (c) $C_{1-3}$alkoxy, (d) $C_{1-3}$alkylthio, (e) CN, (f) $C_{1-2}$fluoroalkyl, (g) $C_{1-3}$alkyl, $R^4$ is selected from the group consisting of hydrogen, $C_{1-3}$alkyl, phenyl and benzyl;

$R^5$ and $R^6$ are each independently selected from the group consisting of:

(a) hydrogen, and (b) $C_{1-3}$alkyl.

Within this sub-group are the compounds wherein $R^1$ is selected from the group consisting of:

(a) $S(O)_2CH_3$, (b) $S(O)_2NH_2$, $R^2$ and $R^3$ are each independently selected from the group consisting of:

(a) hydrogen, (b) halo, (c) $C_{1-2}$alkoxy, (d) $C_{1-2}$alkylthio, (e) CN, (f) $C_{1-2}$fluoroalkyl, and (g) methyl and ethyl.

The invention is illustrated by the compounds of the examples as disclosed herein as well as the compounds of Tables I, II and if.

Alkyl is defined to include linear, branched, and cyclic structures, of the indicated number of carbon atoms, including, but not restricted to, methyl, ethyl, propyl, 2-propyl, n-, i-, s- and t-butyl, pentyl, hexyl, 1,1-dimethylethyl, cyclopropyl, cyclobutyl, cyclopentyl and cyclohexyl.

Alkoxy is intended to include alkoxy groups of the indicated number of carbon atoms of a straight, branched, or cyclic configuration. Examples of lower alkoxy groups include methoxy, ethoxy, propoxy, isopropoxy, cyclopropyloxy, cyclohexyloxy, and the like.

Alkylthio is intended to include alkylthio groups of the indicated numer of carbon atoms of a straight, branched or cyclic configuration. Examples of lower alkylthio groups include methylthio, n-propylthio, isopropylthio, cyclohexylthio, etc. By way of illustration, the propylthio group signifies —$SCH_2CH_2CH_3$. Halo includes F, Cl, Br and I.

Fluoroalkyl includes alkyl groups of the indicated number of carbon atoms of a straight, branched or cyclic configuration, in which one or more hydrogens are replaced by fluorine. Up to the maximum number of hydrogens are replaced, such as in perfluoroalkyl. Examples are —$CHF_2$, $CH_2F$, —$CF_3$, —$CH_2CF_3$, c-pr-$F_5$, c-Hex-$F_{11}$, and the like.

Exemplifying the invention are:

(a) 4-phenyl-5-(4-(methylsulfonyl)phenyl)-1-2-3-thiadiazol-3-oxide, (b) 4-(4-fluorophenyl)-5-(4-(methylsulfonyl)phenyl)-1-2-3-thiadiazol-3-oxide, (c) 4-(3-fluorophenyl)-5-(4-(methylsulfonyl)phenyl)-1-2-3-thiadiazol-3-oxide, (d) 4-(3 .4-di fluorophenyl)-5-(4-(methylsulfonyl)phenyl)-1-2-3-thiadiazol-3-oxide, (e) 5-phenyl-4-(4-(methylsulfonyl)phenyl)-1-2-3-thiadiazol-3-oxide, (f) 4-(3 ,5-di fluorophenyl)-5-(4-(methylsulfonyl)phenyl 1-2-3-thiadiazol-3-oxide, (g) 4-(3-chlorophenyl)-5-(4-(methylsulfonyl)phenyl)-1-2-3-thiadiazol-3-oxide.

(h) 4-(4-methylphenyl)-5-(4-(methylsulfonyl)phenyl)-1-2-3-thiadiazol-3-oxide, (i) 4-(3-methylphenyl)-5-(4-(methylsulfonyl)phenyl)-1-2-3-thiadiazol-3-oxide, (j) 4-(2-methylphenyl)-5-(4-(methylsulfonyl)phenyl)-1-2-3-thiadiazol-3-oxide, (k) 4-(3-fluoro-4-methylphenyl)-5-(4-(methylsulfonyl)phenyl)-1-2-3-thiadiazol-3-oxide, Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In another embodiment, the invention encompasses a pharmaceutical composition comprising a compound of formula I in combination with a pharmaceutically acceptable carrier.

Within this embodiment the invention encompasses pharmaceutical compositions for inhibiting COX-2 and for treating or preventing COX-2 mediated diseases comprising a pharmaceutically acceptable carrier and a non-toxic therapeutically effective amount of compound of Formula I as described above.

In another embodiment, the invention encompasses a method of inhibiting cyclooxygenase, or treating or preventing a cyclooxygenase mediated disease or condition, comprising administering to a patient in need thereof, an effective amount of a compound of formula I.

Preferably the disease or condition is mediated by cyclooxygenase-2.

The pharmaceutical compositions of the present invention comprise a compound of Formula I as an active ingredient or a pharmaceutically acceptable salt thereof in copmbination with a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N- ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follow, references to the compounds of Formula I are meant to also include the pharmaceutically acceptable salts.

The compounds of formula I are useful for the relief of pain, fever and inflammation due to a variety of conditions, e.g., rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

The compounds of formula I also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis).

By virtue of high inhibitory activity against COX-2 and/or its specificity for COX-2 over COX-1, the compounds are useful as an alternative to conventional NSAIDs particularly where such non-steroidal antiinflammatory drugs may be contraindicated, such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, the compounds are useful as a partial or complete substitute for conventional NSAIDs in preparations wherein they are presently co-administered with other agents or ingredients. Thus, in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine.

In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. No. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example, peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppository for rectal administration. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods.

Method A

Compound I can be prepared from an appropriately substituted 2-ethanone. Following the method of Hurd and Mori, the ketones II were treated with an acyl hydrazine in refluxing toluene to form acylhydrazones III. Treatment of these acylhydrazones with thionyl chloride gives the corresponding thiadiazoles. See Hurd, C. D. and Mori, R. I. *J. Am Chem. Soc.* 1955, 77, 5359. The thiadiazoles are oxidized to the corresponding N-oxides using $H_2O_2$/TFA (1:1) at 45° C.

As appreciated by those of skill in the art, the scheme is equally applicable to compounds of formulae IA and IB.

Tables I, II and III illustrate compounds of Formula I, which are representative of the present invention.

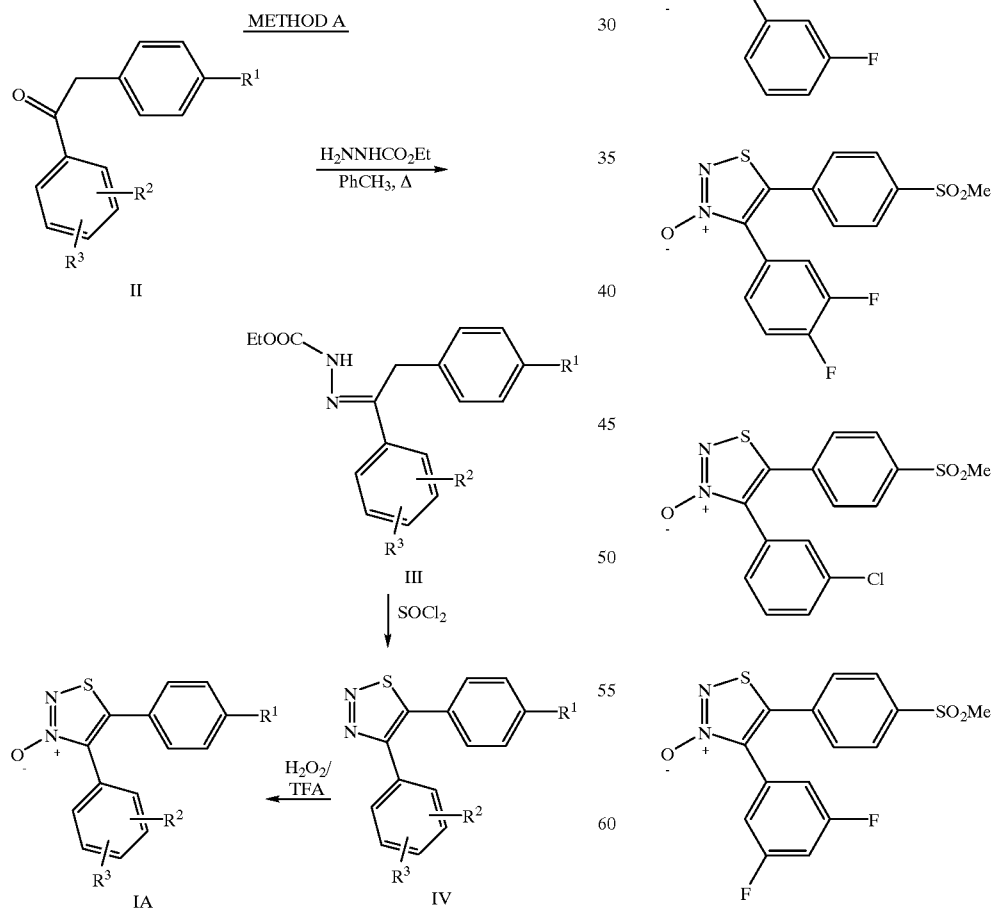

TABLE I

TABLE I-continued

| | Example |
|---|---|
| [structure: 4-methylphenyl / 4-SO2Me phenyl thiadiazole N-oxide] | 7 |
| [structure: 3-methylphenyl / 4-SO2Me phenyl thiadiazole N-oxide] | 8 |
| [structure: 2-methylphenyl / 4-SO2Me phenyl thiadiazole N-oxide] | 9 |
| [structure: 3-methyl-6-fluorophenyl / 4-SO2Me phenyl thiadiazole N-oxide] | 10 |

TABLE II

IA

[structure with substituents $R^1$, $R^2$, $R^3$ on thiadiazole N-oxide scaffold]

| Example | $R^1$ | $R^2$ | $R^3$ |
|---|---|---|---|
| 11 | SO$_2$Me | 3-SMe | H |
| 12 | SO$_2$Me | 4-CF3 | H |
| 13 | SO$_2$NH$_2$ | 4-Me | H |
| 14 | SO$_2$NHMe | 4-CN | H |
| 15 | SO$_2$NH$_2$ | 4-F | H |
| 16 | SO$_2$NH$_2$ | 3-F | 4-F |
| 17 | SO$_2$NH$_2$ | 4-Cl | H |
| 18 | SO$_2$NH$_2$ | H | H |

TABLE III

IB

[structure with substituents $R^1$, $R^2$, $R^3$ on thiadiazole N-oxide scaffold]

| Examples | $R^1$ | $R^2$ | $R^3$ |
|---|---|---|---|
| 19 | SO$_2$Me | H | H |
| 20 | SO$_2$Me | 4-F | H |
| 21 | SO$_2$Me | 3-F | 4-F |
| 22 | SO$_2$Me | 3-Cl | H |
| 23 | SO$_2$NH$_2$ | H | H |
| 24 | SO$_2$NH$_2$ | 4-F | H |
| 25 | SO$_2$NH$_2$ | H | H |

Assays for Determining Biological Activity

Utility of the compound of Formula I can be demonstrated using the following assays to determine their COX-2 inhibiting activity.

INHIBITION OF CYCLOOXYGENASE ACTIVITY

Compounds were tested as inhibitors of cyclooxygenase activity in whole cell cyclooxygenase assays. Both of these assays measured prostaglandin $E_2$ synthesis in response to arachidonic acid, using a radioimmunoassay. Cells used for these assays were human osteosarcoma 143 cells (which specifically express COX-2) and human U-937 cells (which specifically express COX-1). In these assays, 100% activity is defined as the difference between prostaglandin $E_2$ synthesis in the absence and presence of arachidonate.

Whole Cell Assays

For cyclooxygenase assays, osteosarcoma cells are cultured in I mL of media in 24-well multidishes (Nunclon) until confluent (1–2×10$^5$ cells/well). U-937 cells are grown in spinner flasks and resuspended to a final density of 1.5×10$^6$ cells/mL in 24-well multidishes (Nunclon). Following washing and resuspension of osteosarcoma and U-937 cells in 1 mL of HBSS, 1 $\mu$L of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 $\mu$L of this diluted solution is added to the cells to give a final arachidonic acid concentration of 10 $\mu$M. Control samples are incubated with ethanol vehicle instead of arachidonic acid. Samples are again gently mixed and incubated for a further 10 min at 37° C. For osteosarcoma cells, reactions are then stopped by the addition of 100 $\mu$L of 1N HCl with mixing and by the rapid removal of the solution from cell monolayers. For U-937 cells, reactions are stopped by the addition of 100 $\mu$L of 1N HCl with mixing. Samples are then neutralized by the addition of 100 $\mu$L of 1N NaOH and PGE$_2$ levels measured by radioimmunoassay.

Assay of Cox-1 Activity from U937 microsomes

U937 cell are pelleted by centrifuhation at 500×g for 5 min and washed once with phosphate-buffered saline and repelleted. Cells are resuspended in homogenization buffer consisting of 0.1 M Tris-HCl, pH 7.4., 10 mM EDTA, 2 µg/ml leupeptin, 2 µg/ml soybean trypsin inhibitor, 2 µg/ml aprotinin and 1 µM phenyl methyl sulfinyl fluoride. The cell suspension is sonicated 4 times for 10 sec and is centrifuged at 10,000×g for 10 min at 4° C. The suspension is centrifuged at 100,000×g for 1 hr at 4° C. The 100,000×g microsomal pellet is resuspended in 0.1 M Tris- HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 µg/ml in 0.1 M Tris-HCl buffer, pH 7.4 containing 10 mM EDTA, 0.5 mM phenol, 1 mM reduced glutathione and 1 µM hematin. Assays are performed in duplicate in a final volume of 250 µl. Initally, 5 µl of DMSO vehicle or drug in DMSO are added to 20 µl of 0.1 M Tris-HCl buffer, pH 7.4 containing 10 mM EDTA in wells of 96-deepwell polypropylene titre plate. 200 µl of the microsomal preparation are then added and pre-incubated for 15 min at room temperature before addition of 25 Sal of arachidinic acid in 0.1 M Tris-HCl and 10 mM EDTA, pH 7.4. Samples are incubated for 40 min at room temperature and the reaction is stopped by the addition of 25 µl of 1N HCL. Samples are neutralized with 25 µl 1N NaOH prior to quantitation of $PGE_2$ content by radioimmunoassay (Dupont-NEN or Amersham assay kits). Cyclooxygenase activity is defined as the difference between $PGE_2$ levels in the samples incubated in the presence of aracidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2. See Copeland et al (1994) Proc. Natl. Acad. Sci. 91, 11202–11206).

Recombinant COX-2 is purified from Sf9 cells as previously described (Percival et al (1994) Arch. Biochem. Biophys. 15. 111–118). The assay mixture (180 µl) contains 100 mM sodium phosphate, pH 6.5, 2mM genapol X-100, 1µM hematin, 1 mg/ml gelatin, 80–100 units of purified enzyme (one unit of enzyme is defined as the amount of enzyme required to produce an O.D. change of 0.001/min at 610 nm) and 4 µl of the test compound in DMSO. The enzyme is pre-incubated at room temperature (22° C.) for 15 min prior to initiation of the enzymatic reaction by the addition of 20 µl of a sonicated solution of 1 mM arachidonic acid (AA) and 1 mM TMPD in assay buffer (without enzyme or hematin). The enzyme activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the percent inhibition. $IC_{50}$ values are derived from 4-paramater least squares non-linear regression analysis of the log-dose vs percent inhibition plot.

RAT PAW EDEMA ASSAY

Protocol

Male Sprague-Dawley rats (150–200 g) were fasted overnight and were given, po, either vehicle (1% methocel or 5% Tween 80), or a test compound. One hr later, a line was drawn using a permanent marker at the level above the ankle in one hind paw to define the area of the paw to be monitored. The paw volume ($V_0$) was measured using a plethysmometer (Ugo-Basile, Italy) based on the principle of water displacement. The animals were then injected subplantarly with 50 ,l of 1% carrageenan solution in saline (FMC Corp, Maine) into the paw using an insulin syringe with a 25-gauge needle (i.e., 500 µg carrageenan per paw). Three hr later, the paw volume ($V_3$) was measured and the increases in paw volume ($V_3$-$V_0$) were calculated. The animals were sacrificed by $CO_2$ asphyxiation and the absence or presence of stomach lesions scored. Data were compared with the vehicle-control values and percent inhibition calculated. $ED_{50}$ values were used for comparison. All treatment groups were coded to eliminate observer bias.

NSAID-INDUCED GASTROPHATHY IN RATS

Rationale

The major side effect of conventional NSAIDs is their ability to produce gastric lesions in man. This is believed to be due to the inhibition of COX-1 in the gastrointestinal tract. Rats are particularly sensitive to the actions of NSAIDS. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound, either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose.

$^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 ,uCi of sodium $^{51}$chromate for 30 min at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 µCi) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard NSAIDs. This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocel or 5% Tween 80 in $H_2O$ vehicles, (3 mL/kg b.i.d.) or test compounds at doses from 1–100 mg/kg b.i.d. for 5 days. Intravenous $^{51}Cr$ (5 µCi/kg in 1 ml/kg PBS) is administered 1 h after the last drug/vehicle dose, and feces collected for 24 h in a metabolism cage and assessed for excreted $^{51}$Cr by gamma- counting. Venous blood is sampled 1 h and 8 h after the last drug dose, and plasma concentrations of drug measured by RP-HPLC.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood was collected in heparinized tubes by venipuncture from both male and female volunteers. The subjects had no apparent inflammatory conditions and had not taken any NSAIDs for at least 7 days prior to blood collection. Plasma was immediately obtained from a 2 mL blood aliquot to use as blank (basal levels of $PGE_2$). The remaining blood was incubated with LPS (100 µg/ml final concentration, Sigma Chem, #L-2630 from *E. coli*; diluted in 0.1% BSA-Phosphate buffered saline) for 5 minutes at room temperature. Five hundred µL aliquots of blood were incubated with either 2 SAL vehicle (DMSO) or 2 µL of a test compound at final concentrations varying from 10 nM to 30 µM for 24 hours at 37° C. At the end of the incubation, the blood was centrifuged at 12,000×g for 5 minutes to obtain plasma. Protein in the plasma is precipitated by mixing a 100 µL aliquot of plasma with 400 µL of methanol. The supernatant was assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood was collected into vacutainer tubes containing no anticoagulants. Aliquots of 500 µL were immediately transferred to siliconized microcentrifuge tubes preloaded with 2 µL of either DMSO or a test compound at final concentrations varying from 10 nM to 30 µM. The tubes were vortexed and incubated at 37° C. for 1 hour to allow blood to clot. Serum was obtained by centrifugation (12,000×g for 5 min). Serum protein is precipitated by mixing a 100 µL aliquot of serum with 400 µL of methanol. The supernatant is obtained and assayed for $TxB_2$ using an enzyme immunoassay kit (Cayman, #519031) according to the manufacturer's instruction.

REPRESENTATIVE BIOLOGICAL DATA

Compounds of the present invention are inhibitors of COX-2 and are thereby useful in the treatment of COX-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, COX-1 or COX-2 and a putative inhibitor. The $IC_{50}$ values represent the concentration of putative inhibitor required to return $PGE_2$ synthesis to 50% of that obtained as compared to the uninhibited control.

The results for inhibition of $PGE_2$ production in whole blood and edema inhibition in rat paw may be seen in Table IV. For comparison purposes, the Table also contains data for the conventional NSAID indomethacin.

TABLE IV

Indomethacin

Indomethacin

| Example | COX-1 $IC_{50}$ (µM) | COX-2 $IC_{50}$ (µM) | $ED_{50}$ (mg/kg) |
|---|---|---|---|
| 1 | 38 | 0.6 | 0.9 |
| 2 | 18 | 0.6 | 0.5 |
| 3 | 88 | 1.3 | |
| 4 | 57 | 0.5 | |
| 5 | | 0.5 | 1.5 |
| Indomethacin | 0.2 | 0.2 | 2 |

The following abbreviations have the indicated meanings
Ac=acetyl
AIBN=2.2-azobisisobutyronitrile
Bn=benzyl
DMAP=4-(dimethylamino)pyricline
DMF=N,N-dimethylformamide
DMSO=dimethyl sulfoxide
$Et_3N$=triethylamine
Fur=furandiyl
HBSS=Hanks balanced salt solution
HWB=human whole blood
KHMDS=potassium hexamethyldisilazane
LDA=lithium diisopropylamide
LPS=lipopolysaccharide
Ms=methanesulfonyl=mesyl
MsO=methanesulfonate=mesylate
NBS=N-bromosuccinimide
NCS=N-chlorosuccinimide
NIS=N-iodosuccinimide
NSAID=non-steroidal anti-inflammatory drug
PCC=pyridinium chlorochromate
PDC=pyridinium dichromate
Ph=phenyl
Phe=benzenediyl
Pye=pyridinediyl
r.t.=room temperature
rac.=racemic
Tf=trifluoromethanesulfonyl=triflyl
TfO=trifluoromethanesulfonate=triflate
Th=2- or 3-thienyl
THF=tetrahydrofuran
Thi=thiophenediyl TLC=thin layer chromatography
Ts=p-toluenesulfonyl=tosyl
TsO=p-toluenesulfonate=tosylate
Tz=1H (or 2H)-tetrazol-5-yl
$C_3H_5$=allyl
$SO_2Me$=methyl sulfone
$SO_2NH_2$=sulfonamide
Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only; (iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet;

br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

EXAMPLE 1

4-PHENYL-5-(4-(METHYLSULFONYL) PHENYL-1-2-3—THIADIAZOL-3-OXIDE

Step 1 1-Phenyl-2-(4-(methylthio)phenyl)ethanone

To a cold (0° C.) solution of N-methoxy-N-methylbenzamide (409 mg, 2.27 mmol) in THF (22mL) was added a THF solution (5.0 mL, 0.5 M) of 4-(methylthio)benzylmagnesium chloride (J.Org. Chem. 42, 1914, 1977). The mixture was stirred at 0° C. for 3 h, $NH_4OAc$ was added and the mixture was extracted with EtOAc. The EtOAc extracts were washed with brine, dried over $MgSO_4$, filtered and concentrated to an oil. Chromatography of the oil on silica gel (eluted with 2.5% EtOAc/toluene) gave 501 mg of the title compound.

Step 2 1-Phenyl-2-(4-(methylsulfonyl)phenyl)ethanone

To a suspension of the product of step 2 (59 g, 243 mmol) in a mixture of $CH_2C_2$ (300 mL), MeOH (1 L), t-BuOH (350 mL) was added a suspension of Oxone™ (248 g, 403 mmol) in 700 mL of $H_2O$. The mixture was stirred for 1 h. Saturated $NaHCO_3$ was added slowly until all solid dissolved. The resulting mixture was extracted with $Et_2O$. The ether extracts were dried ($Na_2SO_4$) and concentrated to give 39.3 g of the title compound.

Step 3: Ethyl-1-((4-(methylsulfonyl)phenyl)methyl)-1-((phenyl)methylidene)hydrazinocarboxylate A mixture of the product of step 2 (1.37 g, 5 mmol), ethyl carbazate (572 mg, 5.5 mmol), and p-toluenesulfonic acid (20 mg) in toluene (30 mL) was refluxed with concomitant removal of water for 5 h. The mixture was cooled to r.t. and the crystallised product was filtered and washed with toluene yielding 1.54 g of the title compound.

Step 4: 4-Phenyl-5-(4-(methylsulfonyl)phenyl-1.2,3-thiadiazole

To the product of step 3 (800 mg, 2.23 mmol) at 0° C. was added $SOCl_2$ (6 mL). The mixture 7was refluxed for 2h. Excess $SOCl_2$ was removed under vaccum. The residue was chromatographed on silica gel, eluted with 40% EtOAc in hexane to give 300 mg of the title compound; m.p. 145–146° C. $^1$HNMR ($CD_3COCD_3$):δ3.18 (s, 3H),7.46 (m, 3H), 7.72 (m, 2H), 7.73 (d, 2H, J=8.2 Hz), 8.03 (d, 2H, J=8.2 Hz)

Step 5: 4-Phenyl-5-(4-(methylsulfonyl)phenyl-1-2-3-thiadiazol-3-oxide

To the product of step 4 (2.35 g, 7.43 mmol) was added TFA (20 mL) and 30% $H_2O_2$ (20 mL). The mixture was warmed to 40° C. for 3 h. The mixture was cooled and diluted with EtOAc. The organic extract was washed with $H_2O$, $Na_2S_2O_4$, and brine and then dried over $MgSO_4$. Concentration of the solvent under vaccum, followed by chromatography of the residual oil gave g of the tiltle compound; m.p. 181–182° C. $^1$HNMR ($CD_3COCD_3$):δ3.17 (s, 3H),7.50 (m, 5H), 7.70 (d, 2H, J=8.5 Hz), 8.04 (d, 2H, J=8.5 Hz).

EXAMPLE 2

4-(4-FLUOROPHENYL)-5-(4-(METHYLSULFONYL)PHENYL-1-2-3-THIADIAZOL-3-OXIDE

Following the same procedure as described in Example 1, the title compound was obtained.
$^1$HNMR ($CD_3COCD_3$):δ3.17 (s, 3H), 7.26 (t, 2H, J=9.0 Hz), 7.60 (dd, 2H, J=5.4 Hz), 7.70 (d, 2H, J=8.6 Hz), 8.03 (d, 2H, J=8.6 Hz).

EXAMPLE 3

4-(3-FLUOROPHENYL)-5-(4-(METHYLSULFONYL)PHENYL-1-2-3-THIADIAZOL-3-OXIDE

Following the same procedure as described in Example 1, the title compound was obtained.
$^1$HNMR ($CD_3COCD_3$):δ3.10 (s, 3H), 7.14 (m, 1H), 7.45 (m, 3H), 7.55 (d, 2H, J=8.5 Hz), 7.98 (d, 2H, J=8.5 Hz).

EXAMPLE 4

4-(3,4-DIFLUOROPHENYL)-5-(4-(METHYLSULFONYL)PHENYL-1-2-3-THIADIAZOL-3-OXIDE

Following the same procedure as described in Example 1, the title compound was obtained.

m.p. 110–111° C.

$^1$HNR (CD$_3$COCD$_3$):δ3.17 (s, 3H), 7.33 (m, 1H), 7.43 (m, 1H), 7.64 (m, 1H), 7.74 (d, 2H, J=8.4 Hz), 8.05 (d, 2H, J=8.4 Hz).

EXAMPLE 5

4-(3-CHLOROPHENYL)-5-(4-(METHYLSULFONYL)PHENYL-1-2-3-THIADIAZOL-3-OXIDE

Following the same procedure as described in Example 1, the title compound was obtained.

m.p. 130–131° C.

$^1$HNMR (CD$_3$COCD$_3$):δ3.17 (s, 3H), 7.40 (m, 1H), 7.42 (m, 1H), 7.55 (m, 1H), 7.67 (m, 1H), 7.72 (d, 2H, J=8.6 Hz), 8.05 (d, 2H, J=8.6 Hz).

EXAMPLE 6

4-(3,5-DIFLUOROPHENYL)-5-(4-(METHYLSULFONYL)PHENYL-1-2-3-THIADIAZOL-3-OXIDE

Following the same procedure as described in Example 1, the title compound is obtained.

m.p. 112–113° C.

$^1$HNMR (CD$_3$COCD$_3$):δ3.18 (s, 3H), 7.23 (m, 3H), 7.75 (d, 2H, J=8.3 Hz), 8.06 (d, 2H, J=8.3 Hz).

EXAMPLE 7

4-(4-METHYLPHENYL)-5-(4-(METHYLSULFONYL)PHENYL-1-2-3-THIADIAZOL-3-OXIDE

Following the same procedure as described in Example 1, the title compound is obtained.

m.p. 183–184° C.

$^1$HNMR (CD$_3$COCD$_3$):δ2.39 (3H, s), 3.18 (3H, s), 7.29 (2H, d), 7.40 (2H, d), 7.70 (2H, d),8.04 (2H, d).

EXAMPLE 8

4-(3-METHYLPHENYL)-5-(4-(METHYLSULFONYL)PHENYL-1-2-3-THIADIAZOL-3-OXIDE

Following the same procedure as described in Example 1, the title compound is obtained.

m.p. 142–143° C.

$^1$HNMR (CD$_3$COCD$_3$):δ2.33 (3H, s), 3.17 (3H, s), 7.26–7.38 (4H, m), 7.69 (2H, d), 8.02 (2H, d).

EXAMPLE 9

4-(2-METHYLPHENYL)-5-(4-(METHYLSULFONYL)PHENYL-1-2-3-THIADIAZOL-3-OXIDE

Following the same procedure as described in Example 1, the title compound is obtained.

m.p. 188–189° C.

H NMR(CD$_3$COCD$_3$)δ2.18 (3H, s), 3.16 (3H, s), 7.27–7.49 (4H, m), 7.64 (2H, d), 8.00 (2H, d).

EXAMPLE 10

4-(3-FLUORO-4-METHYLPHENYL)-5-(4-(METHYLSULFONYL)PHENYL-1-2-3-THIADIAZOL-3-OXIDE

Following the same procedure as described in Example 1, the title compound is obtained.

$^1$HNMR (CD$_3$COCD$_3$):δ2.04 (s, 3H), 3.18 (s, 3H), 7.17 (m, 1H), 7.35 (m, 2H), 7.73 (d, 2H, J=8.6 Hz), 8.04 (d, 2H, J=8.6 Hz).

EXAMPLE 11

4-(4-(METHYLSULFONYL)PHENYL-5-(PHENYL)-1,2,3-1-2-3-THIADIAZOL-3-OXIDE

Step 1 1-(4-Methylthiophenyl)-2-phenyl-ethanone To a cold (0° C.) solution of phenylacetyl chloride (92.8 g, 0.6 mol) in CHCl$_3$ (1.2 L) was added AlCl$_3$ (80 g, 0.6 mol) in portions. Thioanisole (62.1 g, 0.5 mol) was then added dropwise. The resulting mixture was stirred at r.t. for 1.5 h. The mixture was poured into 4 L of ice and water and extracted with CHCl$_3$. The combined organic extracts were dried over MgSO$_4$, filtered and concentrated. The residue was slurried in 300 mL of 20% EtOAc/hexane, filtered and washed with hexane to give 78 g of the title compound.

Step 2

Starting from the product of step 1, following the same procedure as described in step 2–4 of Example 1, the title compound was obtained.

$^1$HNMR (CD$_3$COCD$_3$):δ3.17 (s, 3H),7.52 (m, 5H), 7.69 (d, 2H, J=8.7 Hz), 8.02 (d, 2H, J=8.7 Hz)

What is claimed is:

1. A compound of Formula I

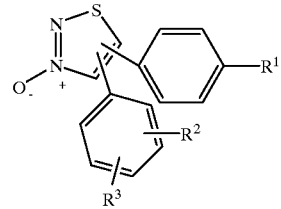

I or a pharmaceutically acceptable salt thereof wherein:

R 1 is selected from the group consisting of:
 (a) S(O)$_2$CH$_3$,
 (b) S(O)$_2$NHR$^4$,
 (c) S(O)$_2$NHCOCF$_3$,
 (d) S(O)(NH)CH$_3$,
 (e) S(O)(NH)NH$_2$,
 (f) S(O)(NH)NHCOCF$_3$,
 (g) P(O)(CH$_3$)OH, and
 (h) P(O)(CH$_3$)NH$_2$, R$^2$ and R$^3$ are each independently selected from the group consisting of:
 (a) hydrogen,
 (b) halo,
 (c) C$_{1-6}$alkoxy,
 (d) C$_{1-6}$alkylthio,
 (e) CN,
 (f) C$_{1-3}$fluoroalkyl,
 (g) C$_{1-6}$alkyl,
 (h) N$_3$,
 (i) —CO$_2$H,
 (j) —CO$_2$—C$_{1-4}$alkyl,
 (k) —C(R$^5$)(R$^6$)—OH,
 (l) —C(R$^5$)(R$^6$)—O—C$_{1-4}$alkyl, and
 (m) —C$_{1-6}$alkyl-CO$_2$—R$^7$;

R$^4$ is selected from the group consisting of H, C$_{1-6}$alkyl, phenyl and benzyl; and R$^5$, R$^6$ and R$^7$ are each independently selected from the group consisting of:

(a) hydrogen, and (b) $C_{1-6}$alkyl.

2. A compound according to claim 1 wherein $R^1$ is selected from the group consisting of:
(a) $S(O)_2CH_3$,
(b) $S(O)_2NHR^4$,
(c) $S(O)_2NHCOCF_3$,
(d) $S(O)(NH)CH_3$,
(e) $S(O)(NH)NH_2$,
(f) $S(O)(NH)NHCOCF_3$, $R^2$ and $R^3$ are each independently selected from the group consisting of:
(a) hydrogen,
(b) halo,
(c) $C_{1-4}$alkoxy,
(d) $C_{1-4}$alkylthio,
(e) CN,
(f) $C_{1-3}$fluoroalkyl,
(g) $C_{1-4}$alkyl,
(h) —$C(R^5)(R^6)$—OH,
(i) —$C(R^5)(R^6)$—O—$C_{1-4}$alkyl, and
(j) —$C_{1-4}$alkyl-$CO_2$—$R^7$;

$R^4$ is selected from the group consisting of hydrogen, $C_{1-6}$alkyl, phenyl and benzyl;

$R^5$, $R^6$ and $R^7$ are each independently selected from the group consisting of:
(a) hydrogen, and
(b) $C_{1-4}$alkyl.

3. A compound according to claim 2 wherein:

$R^1$ is selected from the group consisting of:
(a) $S(O)_2CH_3$,
(b) $S(O)_2NHR^4$,
(c) $S(O)_2NHCOCF_3$,
(d) $S(O)(NH)CH_3$,
(e) $S(O)(NH)NH_2$, $R^2$ and $R^3$ are each independently selected from the group consisting of:
(a) hydrogen,
(b) halo,
(c) $C_{1-4}$alkoxy,
(d) $C_{1-4}$alkylthio,
(e) CN,
(f) $C_{1-3}$fluoroalkyl,
(g) $C_{1-4}$alkyl,
(h) —$C(R^5)(R^6)$—OH,
(i) —$C(R^5)(R^6)$—O—$C_{1-4}$alkyl, and $R^4$ is selected from the group consisting of hydrogen, $C_{1-4}$alkyl, phenyl and benzyl;

$R^5$ and $R^6$ are each independently selected from the group consisting of:
(a) hydrogen, and
(b) $C_{1-4}$alkyl.

4. A compound according to claim 3 of Formula IA

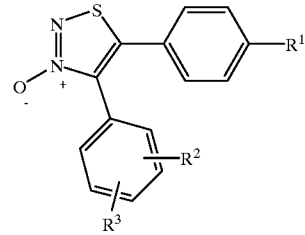

IA wherein:

$R^1$ is selected from the group consisting of:
(a) $S(O)_2CH_3$,
(b) $S(O)_2NHR^4$,
(c) $S(O)(NH)CH_3$,
(d) $S(O)(NH)NH_2$, $R^2$ and $R^3$ are each independently selected from the group consisting of:
(a) hydrogen,
(b) halo,
(c) $C_{1-3}$alkoxy,
(d) $C_{1-3}$alkylthio,
(e) CN,
(f) $C_{1-3}$fluoroalkyl,
(g) $C_{1-3}$alkyl,
(h) —$C(R^5)(R^6)$—O—$C_{1-4}$alkyl, and $R^4$ is selected from the group consisting of hydrogen, $C_{1-3}$alkyl, phenyl and benzyl;

$R^5$ and $R^6$ are each independently selected from the group consisting of:
(a) hydrogen, and
(b) $C_{1-4}$alkyl.

5. A compound according to claim 4 wherein:

$R^1$ is selected from the group consisting of:
(a) $S(O)_2CH_3$,
(b) $S(O)_2NHR^4$,
(c) $S(O)(NH)CH_3$, and $R^2$ and $R^3$ are each independently selected from the group consisting of:
(a) hydrogen,
(b) halo,
(c) $C_{1-3}$alkoxy,
(d) $C_{1-3}$alkylthio,
(e) CN,
(f) $C_{1-2}$fluoroalkyl,
(g) $C_{1-3}$alkyl.

6. A compound according to claim 5 wherein $R^1$ is selected from the group consisting of:
(a) $S(O)_2CH_3$,
(b) $S(O)_2NH_2$, $R^2$ and $R^3$ are each independently selected from the group consisting of:
(a) hydrogen,
(b) halo,
(c) $C_{1-2}$alkoxy,
(d) $C_{1-2}$alkylthio,
(e) CN,
(f) tri-fluoro ethyl or tr-fluoro methyl,
(g) methyl and ethyl, $R^4$ is selected from the group consisting of hydrogen, methyl, ethyl, phenyl and benzyl.

7. A compound according to claim 1 selected from the group consisting of:

(a) 4-phenyl-5-(4-(methylsulfonyl)phenyl)-1-2-3-thiadiazol-3-oxide,
(b) 4-(4-fluorophenyl)-5-(4-(methylsulfonyl)phenyl)-1-2-3-thiadiazol-3-oxide,
(c) 4-(3-fluorophenyl)-5-(4-(methylsulfonyl)phenyl)-1-2-3-thiadiazol-3-oxide,
(d) 4-(3 .4-difluorophenyl)-5-(4-(methylsulfonyl)phenyl)-1-2-3-thiadiazol-3-oxide,
(e) 5-phenyl-4-(4-(methylsulfonyl)phenyl)-1-2-3-thiadiazol-3-oxide,
(f) 4-(3,5-difluorophenyl)-5-(4-(methylsulfonyl)phenyl 1-2-3-thiadiazol-3-oxide,
(g) 4-(3-chlorophenyl)-5-(4-(methylsulfonyl)phenyl)-1-2-3-thiadiazol-3-oxide,
(h) 4-(4-methylphenyl)-5-(4-(methylsulfonyl)phenyl)-1-2-3-thiadiazol-3-oxide,
(i) 4-(3-methylphenyl)-5-(4-(methylsulfonyl)phenyl)-1-2-3-thiadiazol-3-oxide,
(j) 4-(2-methylphenyl)-5-(4-(methylsulfonyl)phenyl)-1-2-3-thiadiazol-3-oxide, and
(k) 4-(3-fluoro-4-methylphenyl)-5-(4-(methylsulfonyl)phenyl)-1-2-3-thiadiazol-3-oxide.

8. A pharmaceutical composition comprising a compound according to claim 1 in combination with a pharmaceutically acceptable carrier.

9. A pharmaceutical composition in accordance with claim 8 for treating cyclooxygenase mediated diseases treated by an active agent that selectively inhibits COX-2 comprising a non-toxic therapeutically effective amount of the compound in combination with a pharmaceutically acceptable carrier.

10. A method of treating a cyclooxygenase mediated disease or condition treated by an active agent that selectively inhibits COX-2 comprising administering to a mammalian patient in need of such treatment a compound according to claim 1 in an amount effective to treat said cyclooxygenase mediated disease.

11. A method of treating inflammation comprising administering to a mammalian patient in need of such treatment a compound according to claim 1 in an amount effective to treat inflammation.

12. A method of treating inflammation in a mammalian patient for which non-steroidal anti-inflammatory drugs may be contra-indicated comprising administering to a patient in need of such treatment a compound according to claim 1 in an amount effective to treat inflammation.

* * * * *